United States Patent [19]
Fisher et al.

[11] Patent Number: 5,290,550
[45] Date of Patent: Mar. 1, 1994

[54] METHOD OF TREATING ASTHMA USING IL-8

[75] Inventors: Robert H. Fisher; W. James Metzger, both of Greenville, N.C.

[73] Assignee: East Carolina University, Greenville, N.C.

[21] Appl. No.: 73,655

[22] Filed: Jun. 7, 1993

Related U.S. Application Data

[63] Continuation of Ser. No. 732,210, Jul. 19, 1991.

[51] Int. Cl.$^5$ .............................................. A61K 37/02
[52] U.S. Cl. ...................................... 424/85.2; 524/2; 524/3; 524/12
[58] Field of Search ................. 424/85.2; 514/2, 3, 514/12

[56] References Cited

U.S. PATENT DOCUMENTS

| | | | |
|---|---|---|---|
| 4,613,500 | 9/1986 | Suzuki et al. | 514/12 X |
| 4,832,012 | 5/1989 | Raabe et al. | 128/200.21 |
| 4,985,242 | 1/1991 | Sekine et al. | 514/2 X |
| 5,011,678 | 4/1991 | Wang et al. | 514/2 X |

FOREIGN PATENT DOCUMENTS

| | | |
|---|---|---|
| 0269455 | 6/1988 | European Pat. Off. |
| WO89/04836 | 6/1989 | PCT Int'l Appl. |
| WO90/06321 | 6/1990 | PCT Int'l Appl. |
| 8904836 | 6/1989 | World Int. Prop. O. |
| 9006321 | 6/1990 | World Int. Prop. O. |

OTHER PUBLICATIONS

P. Collins et al., *Journal of Immunology* 146, 677–684 (1991).
F. Brennan et al., *Eur. J. Immunol.* 20, 2141–2144 (1990).
B. Nickoloff et al., *Am. J. of Path.* 138, 129–140 (1991).
J. Van Damme and G. Opdenakker, *J. Invest. Dermatol.* 95, 90S–93S (1990).
C. Dahinden et al., *J. Exp. Med.* 170 1787–1792 (1989).
T. Stephens, *J. NIH Res.* 3, 60–61 (1991).
C. Herbert et al., *Journal of Immunology* 145, 3033–3040 (1990).
T. Standiford et al., *J. Clin. Invest.* 86, 1945–1953 (1990).
M. Seitz et al., *J. Clin. Invest.* 87, 463–469 (1991).
L. Burrows et al., *Annals New York Academy of Sciences,* 422–424 (1991).
P. Carre et al., *J. Clin. Invest.* 88, 1802–1810 (1991).
W. Holmes et al., *Science* 253, 1278–1280 (1991).
C. Herbert et al., *The Journal of Biological Chemistry* 266, No. 28, 18989–18994 (1991).
H. Nakamura et al., *The Journal of Biological Chemistry* 266, No. 29, 19611–19617 (1991).
"Chemotactic Cytokines: Biology of the Inflammatory Peptide Supergene Family," vol. 305, (Planum Press, New York) (1991).
R. Alam et al., Agonistic-Antagonistic Property of Interleukin 8 on Basophils: Identification of IL–8 as a Potent Inhibitor of Cytokine–Induced Histamine Release *The Journal of Allergy and Clinical Immunology* 87, Abstract (1991).
Science, vol. 246, Dec., 1989, 1601–1603, Gimbrone et al.

*Primary Examiner*—Howard E. Schain
*Attorney, Agent, or Firm*—Bell, Seltzer, Park and Gibson

[57] ABSTRACT

A method of treating asthma in a subject in need of such treatment comprises contacting Interleukin-8 or an active fragment thereof to the respiratory epithelium of the subject. The active agent is preferably human endothelial IL-8, and is preferably contacted to the subject's respiratory epithelium by causing the subject to inhale respirable particles comprised of the active agent.

12 Claims, 6 Drawing Sheets

METHOD OF TREATING ASTHMA USING IL-8

This invention was made with government support under grant number NIH 5 ROI AI26726 from the National Institutes of Health. The government may have certain rights to this invention.

This is a continuation of co-pending application Ser. No. 07/732,210 filed on Jul. 19, 1991.

FIELD OF THE INVENTION

This invention generally relates to the treatment of asthma, and particularly relates to the treatment of asthma with Interleukin-8 agonists.

BACKGROUND OF THE INVENTION

Four years ago we attempted to isolate a protein, produced by platelets, which causes histamine release from human basophils. R. Fisher et al., *J. Allergy Clin. Immunol.* 79, 196 (1987). This platelet-derived histamine releasing factor (PD-HRF) was present in supernatants obtained from washed platelets, and the supernatant was found to induce allergic skin reactions in human asthma patients. M. Weiss et al., J. *J. Allergy Clin. Immunol.* 81, 224 (1988). In order to further define its role in asthma, PD-HRF supernatants were used to challenge normal or allergic asthmatic rabbits by inhalation challenge. While normal rabbits in general were unaffected, asthmatic rabbits developed the typical changes associated with an asthma attack including early and late airway obstruction and increased hyperresponsiveness. W. Metzger et al. *J. Allergy Clin. Immunol.* 85(1) (1990); R. Fisher et al. *J. Allergy Clin. Immunol.* 85(1) (1990).

SUMMARY OF THE INVENTION

The present invention provides a method of treating asthma in a subject in need of such treatment. The method comprises administering an active agent to the subject by contacting the active agent to the respiratory epithelium of the subject. The active agent is either Interleukin- 8 or an active fragments thereof. The active agent is administered to the subject in an effective asthma-combatting amount. The active agent is preferably contacted to the subject's respiratory epithelium by causing the subject to inhale respirable particles (i.e., liquid particles or solid particles) comprised of the active agent.

A second aspect of the present invention is the use of an active agent as given above for the preparation of a medicament for treating asthma.

A third aspect of the present invention is a method of treating fibromyalgia in a subject in need of such treatment. The method comprises administering to the subject an active agent as described above, and in the manner described above, in an effective fibromyalgia-combatting amount. The subject being treated for fibromyalgia may be one also afflicted with and being treated for asthma, or may be treated solely for fibromyalgia.

A fourth aspect of the present invention is the use of an active agent as given above for the preparation of a medicament for treating fibromyalgia.

DETAILED DESCRIPTION OF THE INVENTION

Figure 1:
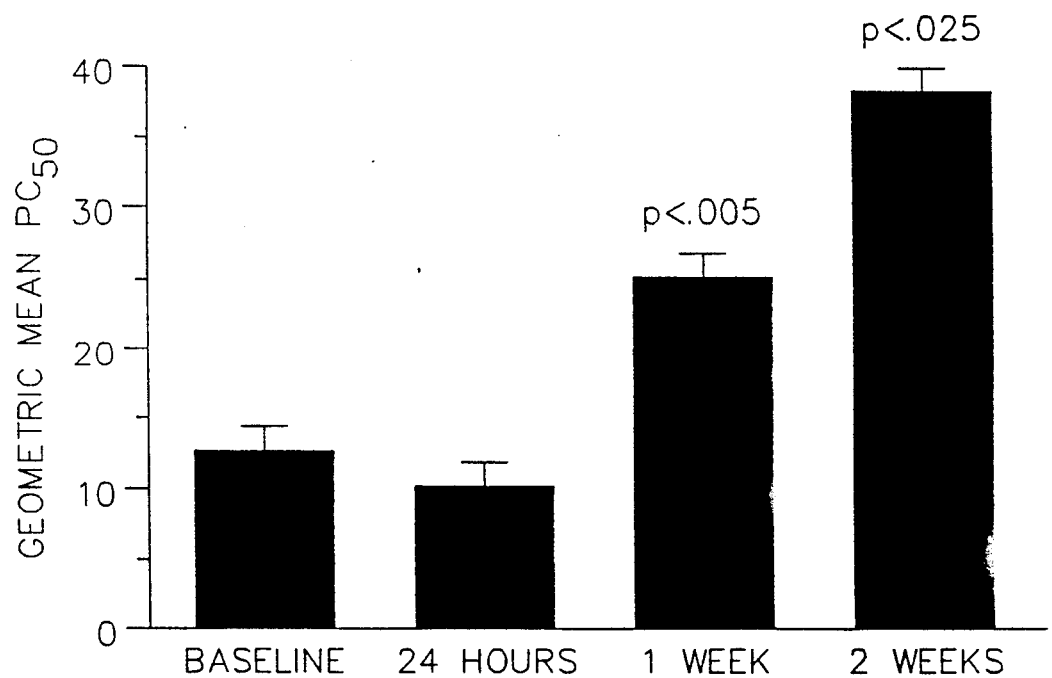
FIG. 1 shows that IL-8 inhalation reverses hyperresponsiveness. Asthmatic rabbits (n=7) were challenged with histamine before IL-8 (baseline), and at indicated times.

Aerosol particles (solid or liquid) for practicing the present invention are preferably particles of respirable size: that is, particles of a size sufficiently small to pass through the mouth and larynx upon inhalation and into the bronchi and alveoli of the lungs. In general, particles ranging from about 1 to 10 microns in size (more particularly, less than about 5 microns in size) are respirable.

The present invention is useful for combatting all types of asthma, including allergic rhinitis. For the treatment of allergic rhinitis the active agent need only reach the subject's nasal epithelia. For this purpose an aqueous solution carrying the active agent may be topically applied to the nasal epithelium in the form of particles, droplets, or solutions.

When used for treating fibromyalgia, the active agent is preferably administered by contacting it the the subject's respiratory epithelia. However, other routes of administration may also be employed when treating this condition, including oral administration and parenteral administration (i.e., subcutaneous injection, intraveneous injection, intramuscular injection).

The term "Interleukin-8" (IL-8) as used herein, means the polypeptide produced by stimulated mammalian peripheral blood lymphocytes, endothelial cells, and monocytes that has been identified previously by names such as neutrophil-activating peptide and neutrophil chemotactic factor. See generally M. Gimbrone et al., Science 246, 1601, 1603 n. 14 (1989). This compound is known. The Interleukin-8 may be of any species of origin, such as ovine, bovine, and human, but is preferably of mammalian origin. Il-8 is produced in various lengths depending upon the cell of origin thereof, but IL-8 originating from any cell type may be employed in practicing the present invention, including blood lymphocytes, endothelial cells, and monocytes, but is preferably obtained from endothelial cells. These compounds are known. See, e.g., M. Gimbrone et al., supra; M. Baggiolini and K. Clemetson, PCT Application WO 90/06321; H. Aschauer and P. Peveri, PCT Application WO 89/04836. Particularly preferred for practicing the present invention is human endothelial cell IL-8, which is commercially available from Genzyme, Inc. Boston, Mass., USA. The IL-8 may be produced by any suitable means, including by recombinant means in cells which do not typically produce IL-8, and by culture of cells which ordinarily produce IL-8.

Active fragments of Interleukin-8 are peptides derived from Interleukin-8 which have N-terminal, C-terminal, or both N-terminal and C-terminal amino acid residues deleted, but retain the biological activity of Interleukin-8 as described herein. Such active fragments may be prepared by enzymatic digestion of IL-8, by direct synthesis, or by genetic engineering procedures.

The amount of active agent administered to the subject will vary depending upon the age, weight, condition of the subject, and the particular disorder or disorders being treated, but is generally from nanograms to 10 micrograms, and is typically an amount ranging from 1 nanogram to 1 microgram. Medicaments can be formulated as discussed below to deliver this quantity of the active agent to the lungs of a patient by inhalation, or to the nasal respiratory epithelium as a topically applied liquid medicament.

Compositions containing the active agent of the present invention may be prepared in either solid or liquid form. Compositions containing respirable dry particles of micronized active agent may be prepared by grinding dry active agent with a mortar and pestle, and then passing the micronized composition through a 400 mesh screen to break up or separate out large agglomerates. Liquid compositions comprise the active agent dispersed in an aqueous carrier, such as sterile pyrogen free saline solution or sterile pyrogen free water. If desired, the composition may be mixed with a propellant to assist in spraying the composition and forming an aerosol thereof. The solid particulate form of the active agent may optionally contain a dispersant which serves to facilitate the formation of an aerosol. A suitable dispersant is lactose, which may be blended with the active agent in any suitable ratio (e.g., a 1 to 1 ratio by weight). The medicament compositions may be provided in unit dosage form, such as in the form of sterile ampoules or pressurized containers.

Active agents of the present invention may be administered per se or in the form of a pharmaceutically acceptable salt. Such pharmaceutically acceptable salts include, but are not limited to, those prepared from the following acids: hydrochloric, hydrobromic, sulphuric, nitric, phosphoric, maleic, salicylic, p-toluenesulfonic, tartaric, citric, methanesulphonic, formic, malonic, succinic, naphthalene-2-sulphonic and benzenesulphonic. Also, pharmaceutically acceptable salts can be prepared as alkaline metal or alkaline earth salts, such as sodium, potassium or calcium salts of a carboxylic acid group.

Liquid aerosols of respirable particles may be administered by any suitable means, such as by nebulizing a liquid composition containing the active agent (e.g., with a jet nebulizer or an ultrasonic nebulizer), and causing the patient to inhale the nebulized composition. Alternatively, patients maintained on a ventilating apparatus can be administered an aerosol of respirable particles by nebulizing the liquid composition and introducing the aerosol into the inspiratory gas stream of the ventilating apparatus, as described in U.S. Pat. No. 4,832,012 to Raabe and Lee (the disclosure of which is to be incorporated herein by reference).

Any solid particulate medicament aerosol generator may be used to practice the present invention, with specific examples being given below. Aerosol generators for administering solid particulate medicaments to a human subject produce particles which are respirable, as explained above, and generate a volume of aerosol containing a predetermined metered dose of a medicament at a rate suitable for human administration. One illustrative type of aerosol generator comprises a chamber having a rotor mounted therein, which rotor carries a gelatin capsule containing a metered dose of dry particle medicament. In use the capsule is pierced, a patient inhales through the chamber, and the rotor is caused to spin at a speed sufficient to dispense the medicament to thereby form an aerosol of dry particles. A second type of illustrative aerosol generator comprises a pressurized canister containing dry particle medicament in a propellant. The propellant is discharged through a metering valve configured to dispense a metered dose of the dry particle medicament into the atmosphere. The propellant evaporates, leaving an aerosol of dry particle medicament.

The present invention is explained in greater detail in the following non-limiting examples.

EXAMPLE 1

Treatment of Rabbits

Materials. Provacholine brand of methacholine was purchased from Roche (Nutley, N.J.), and diluted in 0.9% saline containing 0.4% phenol (Hollister-Steir, Spokane, Wash.). Histamine ediphosphate (Sigma, St. Louis, Mo.) was diluted in saline. Human recombinant endothelial IL-8 (Genzyme, Boston, Mass.) was diluted in phosphate-buffered saline (PBSO containing 0.1% human serum albumin (HSA) as a stock solution of 2 $\mu$g/ml, and frozen in aliquotes at $-80°$ C. until used. This was then further diluted in 0.9% NaCl with 2mM $CaCl_2$ just prior to inhalation. Stock solutions of Ragweed (40,000 PNU, Greer Laboratories Inc., Lenoir, N.C.) and Dermatophagoides farinae (2,500 Allergy Units, Berkeley Biologicals, Berkeley, Calif.) were diluted in saline.

Rabbit Preparation. Pasturella-free New Zealand white rabbits were used for animal studies. Rabbit does were initially obtained commercially, and then litters of rabbits were raised in the animal care facility of East Carolina University School of Medicine. Neonatal rabbits were immunized intraperitoneally within 24 hours of birth with 0.5 ml of 1 mg/ml ragweed (Greer, Lenoir, NC), or 612 AU/ml of *Dermatophagoides farinae*, mixed with 10% kaolin in saline. These immunizations were repeated weekly for the first month, and then biweekly for the next 2-3 months.

Bronchial Measurements. Adult rabbits (2.5-3.5 kg) were anaesthetized and relaxed with a mixture of ketamine hydrochloride (35 mg/kg) (Vance Products, Syracuse, NY) and Acepromazine maleate (1.5 mg/kg) (Aveco Co., Inc., Fort Dodge, Iowa) to permit intubation. Each rabbit was laid supine and intubated with a 4.0 mm endotracheal tube (Mallinckrodt, Inc., Glens Falls, N. Y.) which was attached to a heated Fleisch pneumotachograph (size 00) (DOM Medical Inc., Richmond, Va.) and flow was measured with a Validyne pressure transducer (Validyne Engineering Corp., Northridge, Calif. Model DP-45-16-1927), driven by a Gould carrier amplifier (Model 11-4113, Gould Electronics, Cleveland, Ohio). Pleural pressure was estimated by placing an esophageal balloon in the lower third of the esophagus to obtain maximal pressure changes. Transthoracic pressure was measured by a side-hole connected to the distal end of the tracheal tube. Transpulmonary pressure, the difference between pleural pressure and thoracic pressure, was measured by a Validyne differential pressure transducer. These were attached to a Buxco automated pulmonary mechanics analyzer (Model 6, Buxco Electronics Inc., Sharon, Conn.), and flow was integrated to elicit a continuous tidal volume. Measurements of lung resistance ($R_1$) and dynamic compliance (Cdyn) were calculated at isovolumetric points and zero flow points, respectively, in accordance with known procuedures. See, e.g., R. Giles et al., *Arch. Int. Pharmacodyn. ther.* 194, 213-222 (1971). Bronchial hyperresponsiveness was determined by calculating the dose of histamine (mg/ml) required to reduce the Cdyn by 50% from baseline ($PC_{50}$).

Histamine (0.139-80 mg/ml), ragweed (5 inhalations of 10,000 PNU/ml) or *Dermatophagoides farinae* (as a dose response) were delivered with a DeVilbiss nebulizer (DeVilbiss Co., Somerset, Pa.) for two minutes at two minute intervals for each administration. Aerosols were administered directly to the lungs via the endotracheal tube, during which time lung function was not assessed. IL-8 (1, 10 and 100 ng/ml) was administered with a handheld DeVilbiss nebulizer. The aerosols were determined previously to be composed of droplets, 80% of which were less than 5 microns in diameter, and 1 ml of solution was delivered to the lung.

Bronchoalveolar Lavage. Rabbits were lavaged by inserting a catheter (extenal diameter, 2.4 mm) gently into the airways until it was wedged. 3 cc of normal saline, buffered with 10% rabbit serum albumin, was injected into the catheter, and gently suctioned through sterile trap. Approximately 50% of the injected fluid was obtained using the Shandon Cytospin II ™ (Sewickley, Pa.). Cells obtained in this manner were stained with Lensur's stain.

Experimental Protocol. In essence, 2 protocols were followed for the studies described in this Example. In the first case, 3 allergic rabbits with mild airway hyperresponsiveness were anesthetized, intubated, and subjected to an aerosol challenge of increasing concentrations of IL-8 (1, 10 and 100 ng/ml) in saline with 2 mM $CaCl_2$. Cdyn and $R_1$, both measures of obstruction, were measured for six hours (every 15 minutes for one hour, then every 30 minutes). Non-specific hyperresponsiveness, measured by the $PC_{50}$, was measured prior to challenge, 24 hours later, and at 1 week and 2 weeks. Bronchalveolar lavage was performed prior to challenge and at 1, 3, 6 and 24 hours to assess the effect of IL-8 inhalation on cell types.

Since IL-8 inhalation appeared to effect these parameters, a second protocol was subsequently incorporated into our studies to determine if IL-8 inhalation had a protective effect with regard to allergen exposure. Therefore, 4 allergic asthmatic rabbits were subjected to allergen inhalation followed in 8 days by IL-8 inhalation. Cdyn, $R_L$ and $PC_{50}$ were measured as before. Two weeks later these rabbits were then retreated with IL-8 (100 ng/ml) by aerosol, and rechallenged with allergen 30 minutes later. Thus, allergen challenge with and without IL-8 pretreatment could be compared. A separate group of 4 allergic rabbits were challenged with human serum albumin (HSA) in saline as a control for comparison.

Results. IL-8 inhalation in three asthmatic rabbits caused a rapid improvement in compliance, which was significantly greater than that seen in the HSA control rabbits at 15 minutes, one hour and six hours (data not shown). However, when results obtained with the first three rabbits were pooled with those obtained for the next four, no significant difference was observed between IL-8 and saline (data not shown). The second group of rabbits, which had been recently challenged with allergen, had greater baseline hyperresponsiveness and possibly more ongoing inflammation. Thus the acute effects of IL-8 on compliance may not be as readily detected once inflammation is already present.

Airway resistance is a more direct reflection of airway diameter. Saline inhalation results in a gradual increase in $R_L$. IL-8 dissolved in saline appears to delay the onset of this increase in resistance, and significantly improves resistance during the first hour (data not shown).

IL-8's effects on airway hyperresponsiveness are more dramatic. The pooled results of all seven rabbits is shown in FIG. 1. The geometric mean of $PC_{50}$ in mg/ml histamine was calculated immediately before IL-8 and following inhalation. At baseline, the mean $PC_{50}$ was $12.3 \pm 1.2$ mg/ml and 24 hours after IL-8 treatment, the $PC_{50}$ was unchanged at $10.1 \pm 1.5$. However, within a week, the $PC_{50}$ has more than doubled to $25.6 \pm 1.1$ mg/ml, and after two weeks, had continued to improve to three times baseline at $37.7 \pm 1.5$ mg/ml. The values at 1 and 2 weeks are essentially the same as those routinely seen with normal, non-asthmatic animals.

Figure 2:
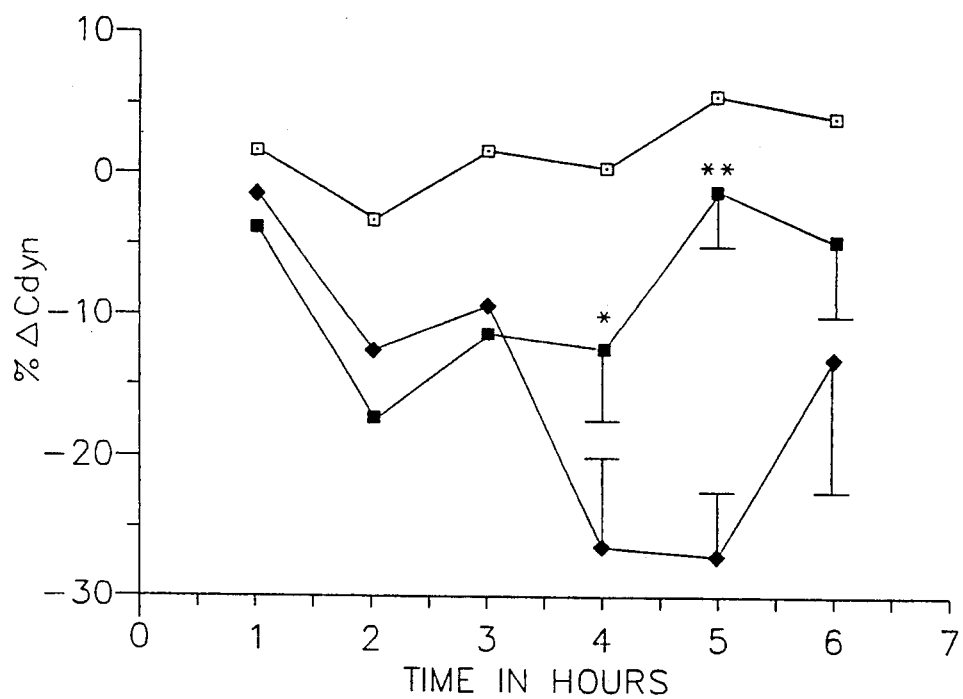
FIG. 2 shows that IL-8 pretreatment inhibits allergen-induced late changes in Cdyn. Asthmatic rabbits premedicated with IL-8 (closed squares, n=4) had a smaller drop in Cdyn compared to premedication with saline for the same rabbits (diamonds)(*p<.1, **p<.005). Inhibition was 73% for hours 4 through 6 (p<.005). For comparison to allergen response, saline challenge (open squares, n=4) is also represented.

While saline inhalation has no effect on compliance, inhalation of allergen reduces compliance, particularly from hours 4 to 6 (FIG. 2). This later onset of obstruction is generally referred to as the asthmatic late-phase, and is associated with the presence of inflammatory cells found in the lung. See J. Kirby et al., *Am. Rev. Respir. Dis.* 136, 379-383 (1987). IL-8 pretreatment inhibits the allergen-induced drop of compliance during the late-phase reaction, particularly at hour 5. Overall, from hours 4 through 6, the % Δ Cdyn for allergen alone was 22% versus 6% for IL-8 pretreatment, a 73% inhibition that was statistically significant (p<.005).

Figure 3:
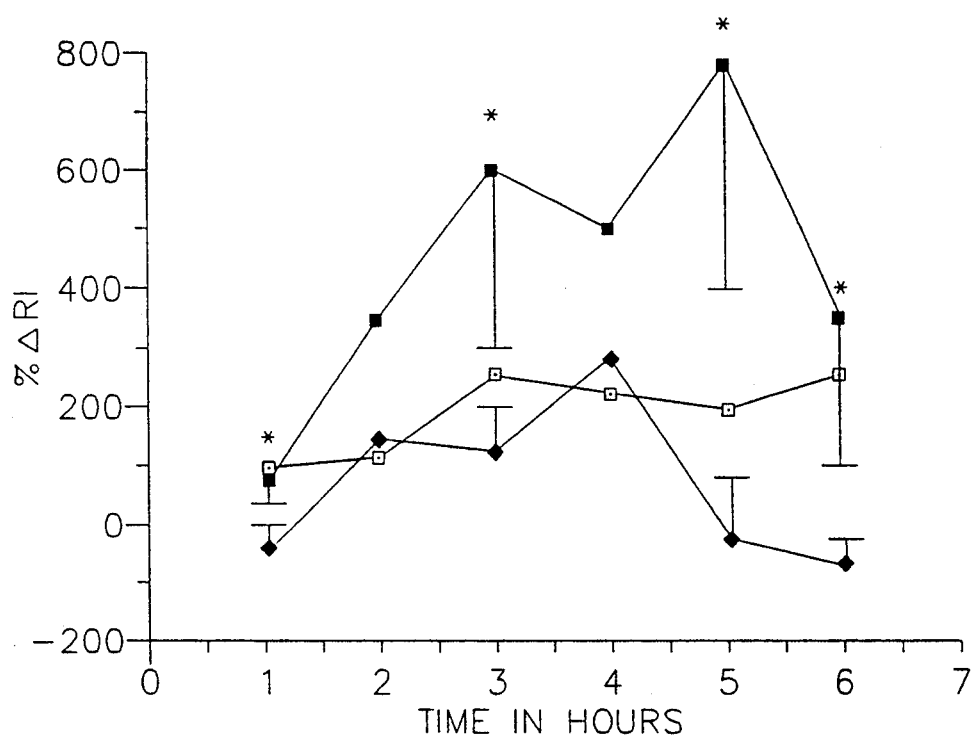
FIG. 3 shows that IL-8 inhalation inhibits allergen-induced increases in resistance. IL-8 pretreatment (diamonds, n=4) blocks the increased resistance attributable to allergen challenge when compared to saline pretreatment (closed squares, n=4)(*p<.05). Compared to saline challenge (open squares, n=4), asthmatic rabbits treated with IL-8 also had smaller increases in resistance at hours 1, 5 and 6 despite their allergen exposure.

IL-8 also blocks the allergen induced increase in resistance (FIG. 3). Compared to allergen challenged rabbits, resistance for IL-8 treated rabbits was significantly less at hours 1, 3, 5, and 6. In fact, resistance was even less than saline challenged rabbits at hours 1 and 6. For hours 4 through 6, the % Δ in resistance for rabbits challenged with allergen alone versus IL-8 pretreated rabbits was 550 versus 82%, p<.025.

Figure 4:
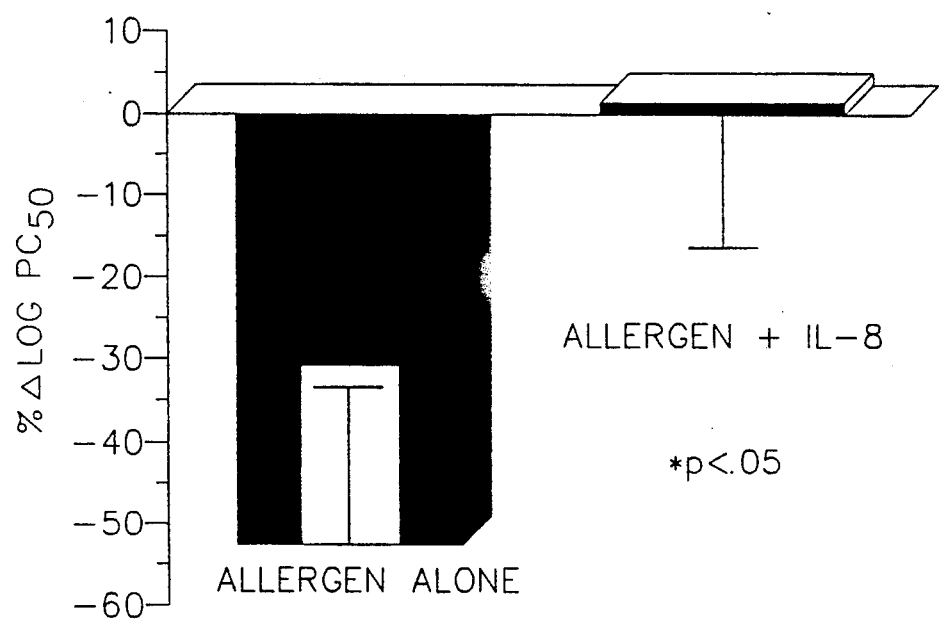
FIG. 4 shows that IL-8 blocks allergen-induced increases in hyperresponsiveness. $PC_{50}$ 24 hours after allergen challenge was compared to baseline. IL-8 pretreatment (n=4) prevented the increase in hyperresponsiveness seen when rabbits were not pretreated (p<.05).

IL-8 pretreatment not only blocks allergen induced obstructive changes, but also prevents the subsequent increase in airway hyperresponsiveness after allergen exposure. As shown in FIG. 4, compared to baseline, allergen exposure results in a 50% drop in the log of PC$_{50}$ within 24 hours when rabbits were not pretreated with IL-8. However, no increase in hyperresponsiveness is seen with IL-8 pretreatment (p<.05).

Figure 5:
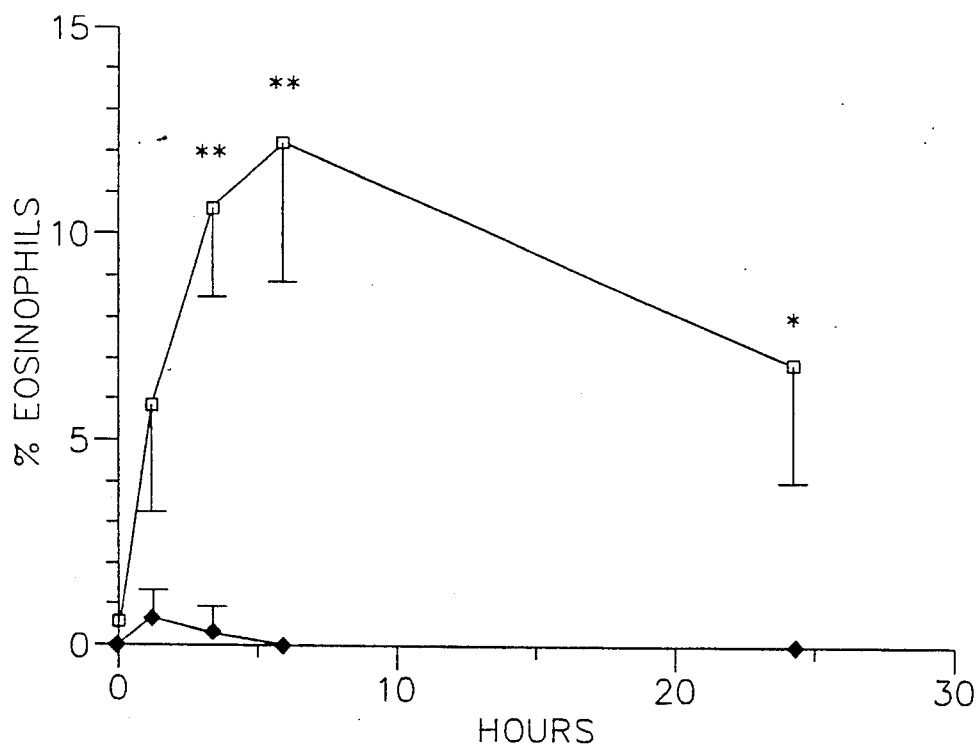
FIG. 5 shows that IL-8 pretreatment blocks allergen-induced bronchial eosinophilia. Pretreatment (diamonds, n=4) blocked the eosinophil influx compared to saline pretreatment (open squares)(*p<.05, **p<.01).

Hyperreactivity may be associated with an influx of eosinophils, see J. Kirby et al., supra, which in turn cause inflammatory damage to the lung. G. Gleich, *NER Allergy Proc.* 7, 421 (1986). Analysis of Bronchalveolar lavage samples from rabbits shows that IL-8 pretreatment completely blocks the influx of eosinophils into the lung that is associated with allergen challenge (FIG. 5).

EXAMPLE 2

Treatment of Humans

A human volunteer with symptoms of allergic rhinitis and asthma, underwent methacholine challenge to assess non-specific hyperresponsiveness, and four hours later received 1 ml of a sterile saline solution containing 100 nanograms of human endothelial IL-8 with 2mM CaCl$_2$ by aerosol inhalation with a DeVilbiss nebulizer. Methacholine challenge was repeated 24 hours later, and again at 1 week and 2 weeks. Methacholine was administered as 5 breaths, 20 psi, using a Rosenthal-French dosimeter (Laboratory for Applied Immunology, USA) at increasing concentrations of 0.039, 0.078, 0.156, 0.312, 0.625, 1.25, 2.5, 5.0, 10 and 25 mg/ml, or until there was a 20% reduction of the forced expiratory volume of 1 second (FEV$_1$) FEV was determined using a computerized spirometer (S&M Instrument Co., Doylestown, Pa.). FEV1 was also recorded prior to IL-8 challenge, and 1, 3, and 24 hours after challenge to determine acute the effects of IL-8 on airflow.

Figure 6:
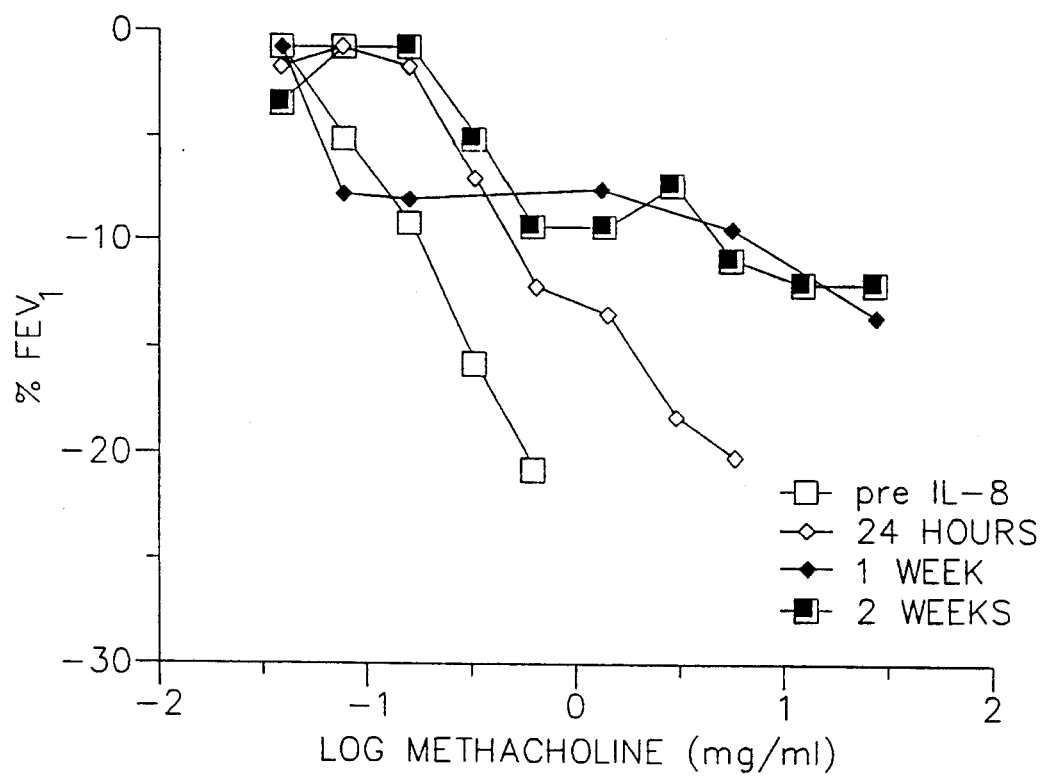
FIG. 6 shows that a single inhalation treatment with IL-8 in a human asthma patient results in progressive and dramatic improvement of airway hyperresponsiveness. $PC_{20}$'s (concentration of methacholine necessary to cause a 20% reduction in $FEV_1$) calculated from dose response curves are: pretreatment 0.72 mg/ml; 24 hours after treatment. 4.27 mg/ml; 1 week 631 mg/ml; and 2 weeks 1, 585 mg/ml).

The effect seen in the human study was similar to that seen in the rabbit study. As depicted in FIG. 6, inhalation of IL-8 shifts the methacholine dose response curve indicating an improvement in airway hyperresponsiveness within 24 hours. The effect is both dramatic and lasts for 2 weeks. IL-8 inhalation did not acutely alter FEV$_1$ in this patient, whose baseline value was already 99% of predicted for age and height. However, rhinitis symptoms were subjectively improved within 24 hours. The subject also had symptomatic resolution of fibromyalgia for two weeks after IL-8 treatment.

The foregoing examples are illustrative of the present invention, and are not to be construed as limiting thereof. The invention is defined by the following claims, with equivalents of the claims to be included therein.

That which is claimed is:

1. A method of treating asthma in a subject in need of such treatment, comprising contacting an active agent selected from the group consisting of Interleukin-8 and active fragments thereof to the respiratory epithelium of said subject, said active agent being administered in an effective asthma-combatting amount.

2. A method according to claim 1, wherein said active agent is carried by a pharmaceutically acceptable carrier.

3. A method according to claim 1, wherein said active agent is carried by a pharmaceutically acceptable liquid carrier.

4. A method according to claim wherein said Interleukin-8 is human Interleukin-8.

5. A method according to claim 1, wherein said active agent is administered to said subject in an amount ranging from 0.1 nanograms to 10 micrograms.

6. A method according to claim 1, wherein said active agent is administered to said subject in an amount ranging from 1 nanogram to 1 microgram.

7. A method of treating asthma in a subject in need of such treatment, comprising administering to the subject by inhalation respirable particles comprised of an active agent selected from the group consisting of Interleukin-8 and active fragments thereof, said active agent being administered in an effective asthma-combatting amount.

8. A method according to claim 7, wherein said respirable particles are liquid particles.

9. A method according to claim 7, wherein said respirable particles are solid particles.

10. A method according to claim 7, wherein said Interleukin-8 is human Interleukin-8.

11. A method according to claim 7, wherein said active agent is administered to said subject in an amount ranging from 0.1 nanoqrams to 10 micrograms.

12. A method according to claim 7, wherein said active agent is administered to said subject in an amount ranging from 1 nanogram to 1 microgram.

* * * * *

UNITED STATES PATENT AND TRADEMARK OFFICE
CERTIFICATE OF CORRECTION

PATENT NO. : 5,290,550
DATED : March 1, 1994
INVENTOR(S) : Robert H. Fisher and W. James Metzger It is certified that error appears in the above-identified patent and that said Letters Patent is hereby corrected as shown below:

Column 3, Line 30, after "from" insert --.1 --.

Column 4, Line 44, correct "ediphosphate" to read -- diphosphate --.

Column 5, Line 24, correct "$(R_1)$" to read -- $(R_L)$ --.

Column 5, Line 45, correct "extenal" to read --external--.

Column 5, Line 59, correct "$R_1$" to read -- $R_L$ --.

Column 6, Line 13, correct "IL-8inhalation" to read --IL-8 inhalation--.

Column 7, Line 29, correct "FEV" to read --$FEV_1$--.

Column 7, Line 31, correct "FEVI" to read —FEV1—.

Column 8, line 19, after "claim" add --1,--.

Signed and Sealed this

Fourth Day of October, 1994

Attest:

BRUCE LEHMAN

*Attesting Officer*    *Commissioner of Patents and Trademarks*